US012595403B2

(12) United States Patent
Sawafta et al.

(10) Patent No.: US 12,595,403 B2
(45) Date of Patent: Apr. 7, 2026

(54) THERMAL ENERGY STORAGE COMPOSITIONS AND METHODS OF USING THE SAME

(71) Applicant: PHASE CHANGE ENERGY SOLUTIONS, INC., Greensboro, NC (US)

(72) Inventors: Reyad I. Sawafta, Greensboro, NC (US); Venu Gopal Kuturu, Greensboro, NC (US)

(73) Assignee: Phase Change Energy Solutions, Inc., Greensboro, NC (US)

( * ) Notice: Subject to any disclaimer, the term of this patent is extended or adjusted under 35 U.S.C. 154(b) by 931 days.

(21) Appl. No.: 17/794,113

(22) PCT Filed: Jan. 20, 2021

(86) PCT No.: PCT/US2021/014206
§ 371 (c)(1),
(2) Date: Jul. 20, 2022

(87) PCT Pub. No.: WO2021/150622
PCT Pub. Date: Jul. 29, 2021

(65) Prior Publication Data
US 2023/0050014 A1 Feb. 16, 2023

Related U.S. Application Data

(60) Provisional application No. 62/963,532, filed on Jan. 20, 2020.

(51) Int. Cl.
| | |
|---|---|
| *C09K 5/06* | (2006.01) |
| *A23L 33/125* | (2016.01) |
| *A61K 47/36* | (2006.01) |
| *A61K 47/38* | (2006.01) |
| *C08L 1/28* | (2006.01) |
| *C08L 3/02* | (2006.01) |
| *C08L 3/08* | (2006.01) |
| *C08L 5/04* | (2006.01) |
| *C08L 5/08* | (2006.01) |
| *C08L 5/12* | (2006.01) |

(52) U.S. Cl.
CPC ............ *C09K 5/063* (2013.01); *A23L 33/125* (2016.08); *A61K 47/36* (2013.01); *A61K 47/38* (2013.01); *C08L 1/284* (2013.01); *C08L 3/02* (2013.01); *C08L 3/08* (2013.01); *C08L 5/04* (2013.01); *C08L 5/08* (2013.01); *C08L 5/12* (2013.01); *A23V 2002/00* (2013.01)

(58) Field of Classification Search
CPC ...................................................... C09K 5/063
See application file for complete search history.

(56) References Cited

U.S. PATENT DOCUMENTS

2014/0271928 A1* 9/2014 Rehage .................... A61K 8/34
424/680
2014/0319410 A1* 10/2014 Sawafta ................. C09K 5/063
252/76

FOREIGN PATENT DOCUMENTS

| | | | |
|---|---|---|---|
| JP | H10265769 A | | 10/1998 |
| JP | 2003322409 A | * | 11/2003 |
| JP | 2006043314 A | * | 2/2006 |
| WO | 2007002044 A1 | | 1/2007 |
| WO | 2020023187 A1 | | 1/2020 |

OTHER PUBLICATIONS

Hirano, English machine translation of JP 2003322409A. (Year: 2003).*
Hirose, English machine translation of JP2006043314A. (Year: 2006).*
Masushige, English machine translation of JPH10265769A. (Year: 1998).*
International Search Report and Written Opinion issued in counterpart PCT Application No. PCT/US2021/014206 dated May 6, 2021 (thirteen (13) pages).

* cited by examiner

*Primary Examiner* — Peter F Godenschwager
(74) *Attorney, Agent, or Firm* — Maynard Nexsen PC; John P. Zimmer

(57) ABSTRACT

In one aspect, thermal energy storage compositions are described herein. In some embodiments, a composition comprises 0.5-10 wt. % polysaccharide and 88-99.5 wt. % water, wherein the weight percentages are based on the total weight of the composition. Moreover, in some cases, the composition is shape stable at 20° C. and 1 atm.

28 Claims, No Drawings

THERMAL ENERGY STORAGE COMPOSITIONS AND METHODS OF USING THE SAME

CROSS REFERENCE TO RELATED APPLICATIONS

This application is a 35 U.S.C. § 371 U.S. national phase entry of International Application No. PCT/US2021/014206 having an international filing date of Jan. 20, 2021, which claims priority pursuant to 35 U.S.C. § 119 to U.S. Provisional Patent Application Ser. No. 62/963,532, filed on Jan. 20, 2020, which are hereby incorporated by reference in their entireties.

FIELD

The present disclosure relates to compositions comprising thermal energy storage compositions and to methods of making and using such compositions.

BACKGROUND

In recent years latent heat storage has become increasingly important in a wide array of technologies. Latent heat includes thermal energy released or absorbed during a change of state of a material without a substantial change in the temperature of the material. The change of state can include a phase change such as a solid-liquid, solid-gas, liquid-gas, or solid-solid phase change, including a crystalline solid to amorphous solid phase change or other solid-to-solid phase change.

Due to their latent heat storage properties, phase change materials (PCMs) have found application in a wide array of thermal energy technologies. However, the use of PCMs has been somewhat limited by disadvantages associated with the thermal energy storage capacity and/or form of certain PCMs. For example, some materials suffer from large volume changes and/or flow in a liquid state. Improved compositions are desired for thermal energy storage and other applications.

SUMMARY

In one aspect, compositions for thermal energy storage are described herein which, in some embodiments, may offer one or more advantages over prior compositions. In some embodiments, for example, a composition described herein exhibits a high latent heat during a solid-to-solid or shape-stable transition, thereby providing a composition that is useful in various applications in which shape stability and/or elimination of flow in the "melted" phase are relevant. Such applications can include thermal energy storage and temperature control applications.

A composition described herein, in some cases, comprises 0.5-10 wt. % polysaccharide or polysaccharide component and 88-99.5 wt. % water, wherein the weight percentages are based on the total weight of the composition. Further, in some instances, the composition is shape stable at 20° C. and 1 atm, as described further below. In other embodiments, the composition has a dynamic viscosity of greater than or equal to 300,000 cP at 20° C. and 1 atm. Moreover, in some implementations, the polysaccharide of a composition described herein comprises a cellulose, cellulose ether, starch, seaweed gum or seaweed hydrocolloid (such as an alginate or alginic acid, an agar, or a carrageenan), chitosan, gum Arabic, locust bean gum, guar gum, xanthan gum, or a combination of two or more of the foregoing. Additionally, in some embodiments, any of the foregoing polysaccharides can be functionalized or chemically modified, such as by alkoxylation, alkylation, or other functionalization.

A composition described herein can also comprise or include one or more additional species or components, in addition to water and a polysaccharide. For example, in some cases, a composition described herein further comprises a pH modulator, such an inorganic or organic acid or base. In some instances, the pH modulator lowers the pH of the composition, while in other cases the pH modulator raises the pH of the composition. In still other implementations, a composition described herein further comprises an ionic liquid, a fire retardant, a polymeric material (other than or in addition to the polysaccharide), and/or an antimicrobial material.

In another aspect, methods of controlling temperature and/or storing thermal energy are described herein. In some such embodiments, a method comprises placing a payload in thermal contact with a composition described herein and transferring thermal energy (i) from the composition to the payload, (ii) from the payload to the composition, (iii) from an exterior environment of the payload to the composition, and/or (iv) from the composition to the exterior environment of the payload. In some instances, transferring thermal energy induces or is caused by a phase transition of the composition or a component of the composition. Moreover, in some implementations, the transferred thermal energy is associated with the latent heat of the composition or of a component of the composition. The payload can comprise a food, a pharmaceutical, a biological sample such as blood or tissue, or another product in need of temperature control.

These and other embodiments are described in greater detail in the description which follows.

DETAILED DESCRIPTION

Implementations and embodiments described herein can be understood more readily by reference to the following detailed description and examples. Elements, apparatus, and methods described herein, however, are not limited to the specific implementations presented in the detailed description and examples. It should be recognized that these implementations are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum of 1.0 or more and ending with a maximum value of 10.0 or less, e.g., 1.0 to 5.3, or 4.7 to 10.0, or 3.6 to 7.9. Similarly, as will be clearly understood, a stated range of "1 to 10" should be considered to include any and all subranges beginning with a minimum of 1 or more and ending with a maximum value of 10 or less, e.g., 1 to 6, or 7 to 10, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points of 5 and 10.

I. Compositions

In one aspect, thermal energy storage compositions are described herein. In some embodiments, a composition described herein comprises 0.5-10 wt. % polysaccharide or polysaccharide component, and 88-99.5 wt. % water, based on the total weight of the composition. Moreover, in some cases, such a composition is self-supporting or shape-stable, including at ambient or other moderate temperature and pressure. For example, in some cases, a composition is shape stable (including without support by side walls or a container or the like) at temperatures above 0° C. at 1 atm, such as at one or more temperatures selected from Table I below. Additionally, the relative humidity may be 50%.

TABLE I

| Shape Stable Temperatures of a Composition Described herein at 1 atm |
| --- |
| 0° C. to 100° C. |
| 0° C. to 90° C. |
| 0° C. to 80° C. |
| 0° C. to 70° C. |
| 0° C. to 60° C. |
| 0° C. to 50° C. |
| 0° C. to 40° C. |
| 0° C. to 30° C. |
| 0° C. to 20° C. |
| 10° C. to 100° C. |
| 10° C. to 90° C. |
| 10° C. to 80° C. |
| 10° C. to 70° C. |
| 10° C. to 60° C. |
| 10° C. to 50° C. |
| 10° C. to 40° C. |
| 10° C. to 30° C. |
| 10° C. to 20° C. |
| 20° C. to 100° C. |
| 20° C. to 90° C. |
| 20° C. to 80° C. |
| 20° C. to 70° C. |
| 20° C. to 60° C. |
| 20° C. to 50° C. |
| 20° C. to 40° C. |
| 20° C. to 30° C. |
| 30° C. to 100° C. |
| 30° C. to 90° C. |
| 30° C. to 80° C. |
| 30° C. to 70° C. |
| 30° C. to 60° C. |
| 30° C. to 50° C. |
| 30° C. to 40° C. |
| 40° C. to 100° C. |
| 40° C. to 90° C. |
| 40° C. to 80° C. |
| 40° C. to 70° C. |
| 40° C. to 60° C. |
| 40° C. to 50° C. |

Such a shape stable composition, in some implementations, does not deform or flow substantially under these conditions for more than 1 hour, more than 2 hours, more than 5 hours, or more than 12 hours. In some implementations, the compositions is solid or is shape-stable and does not flow or deform for 1-24 hours, 1-12 hours, 2-18 hours, or 2-6 hours under the conditions described above.

Moreover, in some instances, a composition described herein may have some fluidity, such as may be exhibited by a paste or gel. For example, in some cases, a composition described herein has a dynamic viscosity of greater than or equal to 300,000 cP at 20° C. and 1 atm. A composition described herein may also comprise a network, such as a crosslinked polysaccharide network. Moreover, in some instances, a composition described herein comprises a polysaccharide network including many hydrogen bonds with water. Additionally, not intending to be bound by theory, the water may form a continuous phase within a scaffolding formed by the polysaccharide.

Compositions described herein can have any pH not inconsistent with the objectives of the present disclosure. For example, a composition described herein can have a pH of between about 2 and about 12, such as between about 2 and about 7, between about 7 and about 12, between about 5 and about 7, between about between about 3 and about 7, between about 4 and about 7, between about 5 and about 7, or between about 6 and about 7. Further, a pH of a composition described herein can be between about 7 and about 12, between about 8 and about 12, between about 8 and about 12, between about 9 and about 12, between about 10 and about 12, or between about 11 and about 12. Moreover, a composition described herein may have a pH of between about 7 and about 11, between about 7 and about 10, between about 7 and about 9, or between about 7 and about 8. Additionally, a composition described herein may have a pH between about 5 and about 9, such as between about 5 and about 8, between about 6 and about 9, or between about 6 and about 8, between about 6 and about 7, or between about 7 and about 8. Not intending to be bound by theory, the use of one or more pH modulators can permit a composition described herein to be prepared and/or used across a variety of pH ranges.

Turning now to specific components of compositions described herein, a composition described herein comprises a polysaccharide. Any polysaccharide not inconsistent with the objectives of the present disclosure may be used. For example, natural, synthetic, functionalized, or crosslinked polysaccharides may be used. For example, in some cases, the polysaccharide comprises a cellulose, cellulose ether, starch, seaweed gum or seaweed hydrocolloid (such as an alginate or alginic acid, an agar, or a carrageenan), chitosan, gum Arabic, locust bean gum, guar gum, xanthan gum, galactomannan polysaccharide or a combination of two or more of the foregoing. Further, it is to be understood that any of the foregoing can be functionalized or chemically modified, such as to provide a cellulose ether. In some preferred embodiments, the polysaccharide comprises a hydroxyethyl starch, hydroxyethyl polysaccharide, or hydroxyethylcellulose. In other instances, the polysaccharide comprises a potato starch, corn starch, rice starch, or wheat starch.

A polysaccharide described herein can have any molecular weight not inconsistent with the objectives of the present disclosure. For example, in some embodiments, a polysaccharide has a weight average molecular weight between about 2,000 and about 3,000,000, between about 20,000 and 2,500,000, or between about 100,000 and about 2,000,000. Moreover, in some instances, the polysaccharide is present in the composition in an amount of about 0.5-7 wt. % or in an amount of about 1-5 wt. %.

Additionally, in some cases, the composition is not a solution or colloid of the polysaccharide. Further, in some embodiments, the water is present in an amount of 90-99 wt. % or in an amount of 95-99.5 wt. %, based on the total weight of the composition.

Compositions described herein can further comprise one or more additional components or additives, in addition to a polysaccharide and water. Non-limiting examples of such additives are further described below. Moreover, it is to be understood that such additives can be present in a composition described herein in any amount not inconsistent with the objectives of the present disclosure. For example, in some cases, an additive is present in an amount less than about 10 weight percent, less than about 5 weight percent, less than about 3 weight percent, less than about 2 weight percent or less than about 1 weight percent, based on the total weight of the composition. In other instances, an additive is present in an amount between 0.5 and 10 wt. %, between 0.5 and 5 wt. %, or between 1 and 3 wt. %, based on the total weight of the composition.

In some embodiments, a composition described herein further comprises a pH modulator as an additive. As described above, such a pH modulator can be acidic or basic, in the sense of lowering/decreasing or raising/increasing the pH of the composition (or of a precursor mixture of the composition). For example, in some embodiments, the pH modulator lowers the pH of the composition, compared to what the pH would be if the pH modulator were absent (or of a precursor mixture of the composition). In other instances, the pH modulator raises the pH of the composition, compared to what the pH would be if the pH modulator were absent. Any pH modulator not inconsistent with the objectives of the present disclosure may be used. For example, in some cases, the pH modulator comprises a weak organic acid or a weak organic base. In some such cases, the pH modulator comprises citric acid, a citrate salt (such as mono-, di-, or tri-sodium citrate), lactic acid or a salt of lactic acid. In other embodiments, the pH modulator comprises an inorganic acid or base. Further, in some cases, a composition described herein comprises or contains more than one pH modulator. In some such instances, a composition described herein comprises at least two pH modulators. A first pH modulator, in some embodiments, lowers the pH of the composition. In certain other embodiments, the first pH modulator raises the pH of the composition. Correspondingly, a second pH modulator may be selected to further modify the pH of the composition in combination with the first pH modulator. For example, a second pH modulator may further lower the pH of the composition where the first pH modulator lowers the pH of the composition. Alternatively, a second pH modulator may raise the pH of the composition while the first pH modulator lowers the pH of the composition. Similarly, where the first pH modulator raises a pH of the composition, the second pH modulator may also raise the pH of the composition or may lower the pH of the composition. In certain embodiments, a first pH modulator may be added during a method of preparing or making a composition described herein, and a second pH modulator is subsequently added to raise or lower the pH as desired.

In still other cases comprising an additive, the composition further comprises an ionic liquid. Any ionic liquid not inconsistent with the objectives of the present disclosure may be used. For example, in some cases, an ionic liquid is pyridinium-based. In other instances, the ionic liquid comprises a sugar or sugar alcohol. Non-limiting examples of ionic liquids which may be used in some embodiments described herein include 1-Allyl-3-methylimidazolium bis (trifluoromethylsulfonyl)imide, 1-Allyl-3-methylimidazolium bromide, 1-Allyl-3-methylimidazolium dicyanamide, 1-Allyl-3-methylimidazolium iodide, 1-Benzyl-3-methylimidazolium chloride, 1-Benzyl-3-methylimidazolium hexafluorophosphate, 1-Benzyl-3-methylimidazolium tetrafluoroborate, 1,3-Bis(3-cyanopropyl)imidazolium bis(trifluoromethylsulfonyl)imide, 1,3-Bis(3-cyanopropyl)imidazolium chloride, 1-Butyl-2,3-dimethylimidazolium hexafluorophosphate, 1-Butyl-2,3-dimethylimidazolium tetrafluoroborate, 4-(3-Butyl-1-imidazolio)-1-butanesulfonate, 1-Butyl-3-methylimidazolium acetate, 1-Butyl-3-methylimidazolium chloride, 1-Butyl-3-methylimidazolium dibutyl phosphate, 1-Butyl-3-methylimidazolium hexafluorophosphate, 1-Butyl-3-methylimidazolium nitrate, 1-Butyl-3-methylimidazolium octyl sulfate, 1-Butyl-3-methylimidazolium tetrachloroaluminate, 1-Butyl-3-methylimidazolium tetrafluoroborate, 1-Butyl methylimidazolium thiocyanate, 1-Butyl-3-methylimidazolium tosylate, 1-Butyl methylimidazolium trifluoroacetate, 1-Butyl-3-methylimidazolium trifluoromethanesulfonate, 1-(3-Cyanopropyl)-3-methylimidazolium bis(trifluoromethylsulfonyl)amide, 1-Decyl-3-methylimidazolium tetrafluoroborate, 1,3-Diethoxyimidazolium bis(trifluoromethylsulfonyl)imide, 1,3-Diethoxyimidazolium hexafluorophosphate, 1,3-Dihydroxyimidazolium bis(trifluoromethylsulfonyl)imide, 1,3-Dihydroxy-2-methylimidazolium bis(trifluoromethylsulfonyl)imide, 1,3-Dimethoxy-2-methylimidazolium hexafluorophosphate, 1-Dodecyl-3-methylimidazolium iodide, 1-Ethyl-2,3-dimethylimidazolium tetrafluoroborate, 1-Ethyl-3-methylimidazolium hexafluorophosphate, 1-Ethyl-3-methylimidazolium L-(+)-lactate, 1-Ethyl-3-methylimidazolium 1,1,2,2-tetrafluoroethanesulfonate, 1-Hexyl-3-methylimidazolium bis(trifluormethylsulfonyl) imide, 1-Hexyl-3-methylimidazolium chloride, 1-Hexyl-3-methylimidazolium hexafluorophosphate, 1-Methylimidazolium chloride, 1-Methyl-3-octylimidazolium chloride, 1-Methyl-3-octylimidazolium tetrafluoroborate, 1-Methyl-3-propylimidazolium iodide, 1-Methyl-3-(3,3,4,4,5,5,6,6,7,7,8,8,8-tridecafluorooctyl)imidazolium hexafluorophosphate, 1,2,3-Trimethylimidazolium methyl sulfate, 1-Butyl-4-methylpyridinium chloride, 1-Butyl-4-methylpyridinium hexafluorophosphate, 1-Butylpyridinium bromide, 1-(3-Cyanopropyl)pyridinium chloride, 1-Ethylpyridinium tetrafluoroborate, 3-Methyl-1-propylpyridinium bis(trifluormethylsulfonyl)imide, Cholin acetate, glycol-choline, glycerol-choline, erythritol-choline, threitol-choline, arabitol-choline, xylitol-choline, ribitol-choline, mannitol-choline, sorbitol-choline, dulcitol-choline, iditol-choline, isomalt-choline, maltitol-choline, or lactitol-choline, or a combination of two or more of the foregoing. Additionally, in some embodiments, one or more of the pH modulators of the composition may comprise or include an ionic liquid.

Additionally, in some cases, the composition further comprises a fire retardant. Any fire retardant not inconsistent with the objectives of the present invention may be used. In some embodiments, a fire retardant comprises a foam. Further, in some cases, a fire retardant can comprise an organic composition or an inorganic composition. In some instances, a fire retardant comprises a phosphate, such as ammonium phosphate, trisodium phosphate, triphenyl phosphate, tricresylphosphate, tris(2-chloroethyl)phosphate, tris (2-chloro-1-(chloromethyl)ethyl)phosphate, tris(chloropropyl)phosphate, tris(1,3-dichloro-2-propyl)phosphate, or tetrekis(2-chlorethyl)dichloroisopentyldiphosphate. In some embodiments, a fire retardant comprises aluminum hydroxide and/or magnesium hydroxide.

A fire retardant may also comprise a zeolite. Any zeolite not inconsistent with the objectives of the present disclosure may be used. In some cases, a zeolite comprises a natural zeolite. In other embodiments, a zeolite comprises an artificial zeolite. In some instances, a zeolite comprises a silicate and/or aluminosilicate. In some implementations, a zeolite comprises a composition according to the formula $M_{x/n}$ [(AlO$_2$)$_x$(SiO$_2$)$_y$]·w H$_2$O, where n is the valence of cation M (e.g., Na$^+$, K$^+$, Ca$^+$, or Mg$^{2+}$), w is the number of water molecules per unit cell, and x and y are the total number of tetrahedral atoms per unit cell. Non-limiting examples of zeolites suitable for use in some embodiments described herein include analcime ((K,Ca,Na) AlSi$_2$O$_6$·H$_2$O), chabazite ((Ca,Na$_2$,K$_2$,Mg) Al$_2$Si$_4$O$_{12}$·6H$_2$O), clinoptilolite ((Na,K,Ca)$_{2-3}$ Al$_3$(Al, Si)$_2$Si$_{13}$O$_{36}$·12H$_2$O), heulandite ((Ca,Na)$_{2-3}$ Al$_3$(Al,Si)$_2$Si$_{13}$O$_{36}$·12H$_2$O), natrolite

7

(Na$_2$Al$_2$Si$_3$O$_{10}$·2H$_2$O), phillipsite ((Ca,Na$_2$, K$_2$)$_3$Al$_6$Si$_{10}$O$_{32}$·12H$_2$O), and stilbite (NaCa$_4$(Si$_{27}$Al$_9$) O$_{72}$·28(H$_2$O)).

Moreover, in some instances, a composition described herein further comprises an antimicrobial material. Any antimicrobial material not inconsistent with the objectives of the present disclosure may be used. An antimicrobial material, in some cases, comprises an inorganic composition, including metals and/or metal salts. In some embodiments, for example, an antimicrobial material comprises metallic copper, zinc, or silver or a salt of copper, zinc, or silver. Moreover, in some instances, an antimicrobial material comprising a metal can also provide thermal conductivity modulation. In other embodiments, an antimicrobial material comprises an organic composition, including natural and synthetic organic compositions. In some cases, an antimicrobial material comprises a β-lactam such as a penicillin or cephalosporin. In some implementations, an antimicrobial material comprises a protein synthesis inhibitor such as neomycin. In some embodiments, an antimicrobial material comprises an organic acid, such as lactic acid, acetic acid, or citric acid. In some cases, an antimicrobial material comprises a quaternary ammonium species. A quaternary ammonium species, in some embodiments, comprises a long alkyl chain, such as an alkyl chain having a C8 to C28 backbone. In some instances, an antimicrobial material comprises one or more of benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethyl-ammonium chloride, and domiphen bromide. Additionally, in some embodiments, one or more of a pH modulator and/or an ionic liquid may also be an antimicrobial material.

A composition described herein may also include a polymeric material other than or in addition to a polysaccharide described herein. Any polymeric material not inconsistent with the objectives of the present disclosure may be used. In some embodiments, a polymeric material comprises an organic composition. For example, in some cases, a polymeric material comprises a polyolefin such as polyethylene or polypropylene, a polycarbonate, a polyester, or a polyurethane. In some instances, a polymeric material comprises polyvinyl alcohol (PVA). In certain instances, a polymeric material comprises an acrylic acid-based polymer. For example, in some embodiments, a composition described herein comprises poly(acrylic acid) (PAA) and/or an acrylic acid-based copolymer.

In certain implementations, a composition described herein may further comprise or include a carboxymethyl ether of one or more polysaccharides. For example, in some embodiments, a composition described herein comprises or includes a carboxymethyl ether formed or derived from one or more of the following: cellulose, chitin, chitosan, curdlan, dextran, pullulan, schleroglucan, schizophyllan, starch, amylose, amylopectin, seaweed gum or seaweed hydrocolloid (such as an alginate or alginic acid, an agar, or a carrageenan), gum Arabic, locust bean gum, guar gum, or xanthan gum, or a combination of two or more of the foregoing. Carboxymethyl ethers may also be formed from natural, synthetic, or functionalized polysaccharides Compositions described herein may comprise of combinations of carboxymethyl ethers wherein each carboxymethyl ether is derived from a separate member of the foregoing group of polysaccharides. Additionally, compositions described herein may comprise or include one or more salts of a carboxymethyl ether. For example, in some embodiments, a composition described herein comprises sodium starch glycolate.

It should be noted that, in some alternative embodiments, various components of a composition described herein can be divided into a plurality of distinct or separate compositions. That is, rather than being included in a single composition (which might be called "C"), the components can be divided into two or more compositions (which might be called, for example, "A" and "B"). Moreover, in some instances, two such sub-compositions (such as "A" and "B" compositions) can be combined to form a composition which is the same as or substantially the same as a "single" composition ("C") described hereinabove. Additional components (e.g., additional inorganic and/or organic solids and/or liquids) may also be included in an "A" or "B" composition.

Moreover, in some embodiments, a composition described herein does not comprise a microcapsule or microencapsulation agent and/or is not encapsulated.

II. Methods

In another aspect, methods of controlling temperature and/or methods of storing and/or releasing thermal energy are described herein. For example, in some embodiments, a method described herein comprises placing a payload in thermal contact with a composition described hereinabove. The method further comprises transferring thermal energy (i) from the composition to the payload, (ii) from the payload to the composition, (iii) from an exterior environment of the payload to the composition, and/or (iv) from the composition to the exterior environment of the payload. Moreover, in some cases, transferring thermal energy induces or is caused by a phase transition of the composition or of a component of the composition. Additionally, in some implementations, the transferred thermal energy is associated with the latent heat of the composition or of a component of the composition.

A method described herein can be used to regulate or control the temperature of any payload not inconsistent with the objectives of the present disclosure. For example, in some embodiments, the payload comprises a food, a pharmaceutical, or a biological sample such as blood or biological tissue.

III. Embodiments

Certain implementations of compositions and methods consistent with the present disclosure are provided as follows.

Embodiment 1. A composition comprising:
0.5-10 wt. % polysaccharide;
88-99.5 wt. % water; and
at least one pH modulator,
wherein the weight percentages are based on the total weight of the composition.

Embodiment 2. The composition of embodiment 1, wherein the composition is shape stable at 20° C. and 1 atm.

Embodiment 3. The composition of embodiment 1, wherein the composition has a dynamic viscosity of greater than or equal to 300,000 cP at 20° C. and 1 atm.

Embodiment 4. The composition of any of embodiments 1-3, wherein the polysaccharide is present in an amount of 0.5-7 wt. %.

Embodiment 5. The composition of any of embodiments 1-3, wherein the polysaccharide is present in an amount of 1-5 wt. %.

Embodiment 6. The composition of embodiment 1, wherein the at least one pH modulator comprises a first pH modulator, and the first pH modulator lowers the pH of the composition.

Embodiment 7. The composition of embodiment 6 wherein:

the at least one pH modulator further comprises at least a second pH modulator; and the second pH modulator raises the pH of the composition.

Embodiment 8. The composition of embodiment 1, wherein the at least one pH modulator comprises a first pH modulator, and the first pH modulator raises the pH of the composition.

Embodiment 9. The composition of embodiment 8, wherein:

the at least one pH modulator further comprises at least a second pH modulator; and the second pH modulator lowers the pH of the composition.

Embodiment 10. The composition of any of the preceding embodiments, wherein the water is present in an amount of 90-99 wt. %.

Embodiment 11. The composition of any of the preceding embodiments, wherein the water is present in an amount of 95-99.5 wt. %.

Embodiment 12. The composition of any of the preceding embodiments, wherein the polysaccharide comprises a cellulose, cellulose ether, starch, seaweed gum, chitosan, gum Arabic, locust bean gum, guar gum, xanthan gum, or a combination of two or more of the foregoing.

Embodiment 13. The composition of embodiment 12, wherein the polysaccharide comprises a cellulose or cellulose ether.

Embodiment 14. The composition of embodiment 13, wherein the polysaccharide comprises hydroxyethylcellulose.

Embodiment 15. The composition of embodiment 12, wherein the polysaccharide comprises a starch.

Embodiment 16. The composition of embodiment 15, wherein the polysaccharide comprises a potato starch, corn starch, rice starch, or wheat starch.

Embodiment 17. The composition of embodiment 12, wherein the polysaccharide comprises a seaweed gum.

Embodiment 18. The composition of embodiment 17, wherein the polysaccharide comprises an alginate or alginic acid, an agar, or a carrageenan.

Embodiment 19. The composition of embodiment 12, wherein the polysaccharide comprises a chitosan.

Embodiment 20. The composition of embodiment 12, wherein the polysaccharide comprises gum Arabic, locust bean gum, guar gum, or xanthan gum.

Embodiment 21. The composition of any of the preceding embodiments, wherein the composition further comprises an ionic liquid.

Embodiment 22. The composition of any of the preceding embodiments, wherein the composition further comprises a fire retardant.

Embodiment 23. The composition of any of the preceding embodiments, wherein the composition further comprises an antimicrobial material.

Embodiment 24. The composition of any of the preceding embodiments further comprising a carboxymethyl ether of a polysaccharide.

Embodiment 25. The composition of any of the preceding embodiments further comprising a carboxymethyl ether salt.

Embodiment 26. The composition of embodiment 25, wherein the carboxymethyl ether salt is sodium starch glycolate.

Embodiment 27. The composition of any of the preceding embodiments, wherein a pH of the composition is between 2 and 7.

Embodiment 28. The composition of any of embodiments 1-26, wherein a pH of the composition is between 7 and 12.

Embodiment 29. The composition of any of embodiments 1-26, wherein a pH of the composition is between 5 and 7.

Embodiment 30. A composition comprising:

0.5-10 wt. % polysaccharide; and 88-99.5 wt. % water, wherein the weight percentages are based on the total weight of the composition.

Embodiment 31. The composition of embodiment 30, wherein the composition is shape stable at 20° C. and 1 atm.

Embodiment 32. The composition of embodiment 30, wherein the composition has a dynamic viscosity of greater than or equal to 300,000 cP at 20° C. and 1 atm.

Embodiment 33. The composition of any of embodiments 30-32, wherein the polysaccharide is present in an amount of 0.5-7 wt. %.

Embodiment 34, The composition of any of embodiments 30-32, wherein the polysaccharide is present in an amount of 1-5 wt. %.

Embodiment 35. The composition of any of embodiments 30-34, wherein the water is present in an amount of 90-99 wt. %.

Embodiment 36. The composition of any of embodiments 30-35, wherein the water is present in an amount of 95-99.5 wt. %.

Embodiment 37. The composition of any of embodiments 30-36, wherein the polysaccharide comprises a cellulose, cellulose ether, starch, seaweed gum, chitosan, gum Arabic, locust bean gum, guar gum, xanthan gum, or a combination of two or more of the foregoing.

Embodiment 38. The composition of embodiment 37, wherein the polysaccharide comprises a cellulose or cellulose ether.

Embodiment 39. The composition of embodiment 38, wherein the polysaccharide comprises hydroxyethylcellulose.

Embodiment 40. The composition of embodiment 37, wherein the polysaccharide comprises a starch.

Embodiment 41. The composition of embodiment 40, wherein the polysaccharide comprises a potato starch, corn starch, rice starch, or wheat starch.

Embodiment 42. The composition of embodiment 37, wherein the polysaccharide comprises a seaweed gum.

Embodiment 43. The composition of embodiment 42, wherein the polysaccharide comprises an alginate or alginic acid, an agar, or a carrageenan.

Embodiment 44. The composition of embodiment 37, wherein the polysaccharide comprises a chitosan.

Embodiment 45. The composition of embodiment 37, wherein the polysaccharide comprises gum Arabic, locust bean gum, guar gum, or xanthan gum.

Embodiment 46. The composition of any embodiments 30-45, wherein the composition further comprises a pH modulator.

Embodiment 47. The composition of embodiment 46, wherein the pH modulator lowers the pH of the composition.

Embodiment 48. The composition of embodiment 46, wherein the pH modulator raises the pH of the composition.

Embodiment 49. The composition of any of embodiments 30-48, wherein the composition further comprises an ionic liquid.

Embodiment 50. The composition of any of embodiments 30-49, wherein the composition further comprises a fire retardant.

Embodiment 51. The composition of any of embodiments 30-50, wherein the composition further comprises an antimicrobial material.

Embodiment 52. The composition of any of embodiments 30-51 further comprising a carboxymethyl ether of a polysaccharide.

Embodiment 53. The composition of any of embodiments 30-52 further comprising a carboxymethyl ether salt.

Embodiment 54. The composition of embodiment 53, wherein the carboxymethyl ether salt is sodium starch glycolate.

Embodiment 55. The composition of any of embodiments 30-54, wherein a pH of the composition is between 2 and 7.

Embodiment 56. The composition of any of embodiments 30-54, wherein a pH of the composition is between 7 and 12.

Embodiment 57. The composition of any of embodiments 30-54, wherein a pH of the composition is between 5 and 7.

Embodiment 58. A composition comprising:
  0.5-10 wt. % polysaccharide;
  88-99.5 wt. % water;
  at least one pH modulator; and
  an ionic liquid,
    wherein the weight percentages are based on the total weight of the composition.

Embodiment 59. The composition of embodiment 58, wherein the composition is shape stable at 20° C. and 1 atm.

Embodiment 60. The composition of embodiment 58, wherein the composition has a dynamic viscosity of greater than or equal to 300,000 cP at 20° C. and 1 atm.

Embodiment 61, The composition of any of embodiments 58-60, wherein the polysaccharide is present in an amount of 0.5-7 wt. %.

Embodiment 62. The composition of any of embodiments 58-60, wherein the polysaccharide is present in an amount of 1-5 wt. %.

Embodiment 63. The composition of any of embodiments 58-62, wherein the water is present in an amount of 90-99 wt. %.

Embodiment 64. The composition of any of embodiments 58-63, wherein the water is present in an amount of 95-99.5 wt. %.

Embodiment 65. The composition of any of embodiments 58-64, wherein the polysaccharide comprises a cellulose, cellulose ether, starch, seaweed gum, chitosan, gum Arabic, locust bean gum, guar gum, xanthan gum, or a combination of two or more of the foregoing.

Embodiment 66. The composition of embodiment 65, wherein the polysaccharide comprises a cellulose or cellulose ether.

Embodiment 67. The composition of embodiment 66, wherein the polysaccharide comprises hydroxyethylcellulose.

Embodiment 68. The composition of embodiment 65, wherein the polysaccharide comprises a starch.

Embodiment 69. The composition of embodiment 68, wherein the polysaccharide comprises a potato starch, corn starch, rice starch, or wheat starch.

Embodiment 70. The composition of embodiment 65, wherein the polysaccharide comprises a seaweed gum.

Embodiment 71. The composition of embodiment 70, wherein the polysaccharide comprises an alginate or alginic acid, an agar, or a carrageenan.

Embodiment 72. The composition of embodiment 65, wherein the polysaccharide comprises a chitosan.

Embodiment 73. The composition of embodiment 65, wherein the polysaccharide comprises gum Arabic, locust bean gum, guar gum, or xanthan gum.

Embodiment 74. The composition of any embodiments 58-73, wherein the composition further comprises a pH modulator.

Embodiment 75. The composition of embodiment 74, wherein the pH modulator lowers the pH of the composition.

Embodiment 76. The composition of embodiment 74, wherein the pH modulator raises the pH of the composition.

Embodiment 77. The composition of any of embodiments 58-76, wherein the composition further comprises a fire retardant.

Embodiment 78. The composition of any of embodiments 58-77, wherein the composition further comprises an antimicrobial material.

Embodiment 79. The composition of any of embodiments 58-78 further comprising a carboxymethyl ether of a polysaccharide.

Embodiment 80. The composition of any of embodiments 58-79 further comprising a carboxymethyl ether salt.

Embodiment 81. The composition of embodiment 80, wherein the carboxymethyl ether salt is sodium starch glycolate.

Embodiment 82. The composition of any of embodiments 58-81, wherein a pH of the composition is between 2 and 7.

Embodiment 83. The composition of any of embodiments 58-81, wherein a pH of the composition is between 7 and 12.

Embodiment 84. The composition of any of embodiments 58-81, wherein a pH of the composition is between 5 and 7.

Embodiment 85. A method of controlling temperature and/or storing thermal energy, the method comprising:
  placing a payload in thermal contact with the composition of any of embodiments 1-84;
  transferring thermal energy (i) from the composition to the payload, (ii) from the payload to the composition, (iii) from an exterior environment of the payload to the composition, and/or (iv) from the composition to the exterior environment of the payload.

Embodiment 86. The method of embodiment 85, wherein transferring thermal energy induces or is caused by a phase transition of the composition or a component of the composition.

Embodiment 87. The method of embodiment 85 or embodiment 86, wherein the transferred thermal energy is associated with the latent heat of the composition or a component of the composition.

Embodiment 88. The method of any of embodiments 85-87, wherein the payload comprises a food, a pharmaceutical, or a biological sample.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:
1. A composition comprising:
  0.5-10 wt. % polysaccharide;
  88-99.5 wt. % water; and
  at least one pH modulator, wherein the weight percentages are based on the total weight of the composition;

wherein the composition is shape stable at 20° C. and 1 atm; and wherein the at least one pH modulator comprises citric acid, a citrate salt, lactic acid or a salt of lactic acid.

2. The composition of claim 1, wherein the composition has a dynamic viscosity of greater than or equal to 300,000 cP at 20° C. and 1 atm.

3. The composition of claim 1, wherein the polysaccharide is present in an amount of 0.5-7 wt. %.

4. The composition of claim 1, wherein the polysaccharide is present in an amount of 1-5 wt. %.

5. The composition of claim 1, wherein the at least one pH modulator comprises a first pH modulator, and the first pH modulator lowers the pH of the composition.

6. The composition of claim 5 wherein:
the at least one pH modulator further comprises at least a second pH modulator; and
the second pH modulator raises the pH of the composition.

7. The composition of claim 1, wherein the at least one pH modulator comprises a first pH modulator, and the first pH modulator raises the pH of the composition.

8. The composition of claim 7, wherein:
the at least one pH modulator further comprises at least a second pH modulator; and
the second pH modulator lowers the pH of the composition.

9. The composition of claim 1, wherein the water is present in an amount of 90-99 wt. %.

10. The composition of claim 1, wherein the water is present in an amount of 95-99.5 wt. %.

11. The composition of claim 1, wherein the polysaccharide comprises a cellulose, cellulose ether, starch, seaweed gum, chitosan, gum Arabic, locust bean gum, guar gum, xanthan gum, or a combination of two or more of the foregoing.

12. The composition of claim 11, wherein the polysaccharide comprises a cellulose or cellulose ether.

13. The composition of claim 12, wherein the polysaccharide comprises hydroxyethylcellulose.

14. The composition of claim 11, wherein the polysaccharide comprises a starch.

15. The composition of claim 14, wherein the polysaccharide comprises a potato starch, corn starch, rice starch, or wheat starch.

16. The composition of claim 11, wherein the polysaccharide comprises a seaweed gum.

17. The composition of claim 16, wherein the polysaccharide comprises an alginate or alginic acid, an agar, or a carrageenan.

18. The composition of claim 11, wherein the polysaccharide comprises a chitosan.

19. The composition of claim 11, wherein the polysaccharide comprises gum Arabic, locust bean gum, guar gum, or xanthan gum.

20. The composition of claim 1, wherein the composition further comprises an ionic liquid.

21. The composition of claim 1, wherein the composition further comprises a fire retardant.

22. The composition of claim 1, wherein the composition further comprises an antimicrobial material.

23. The composition of claim 1 further comprising a carboxymethyl ether of a polysaccharide.

24. The composition of claim 1 further comprising a carboxymethyl ether salt.

25. The composition of claim 24, wherein the carboxymethyl ether salt is sodium starch glycolate.

26. The composition of claim 1, wherein a pH of the composition is between 2 and 7.

27. The composition of claim 1, wherein a pH of the composition is between 7 and 12.

28. The composition of claim 1, wherein a pH of the composition is between 5 and 7.

* * * * *